(12) United States Patent
Candray et al.

(10) Patent No.: US 6,783,520 B1
(45) Date of Patent: Aug. 31, 2004

(54) CONNECTOR HOLDER FOR A FLUID CONNECTION SYSTEM

(75) Inventors: Adolfo M. Candray, Mc Allen, TX (US); Conor Curtin, N.Y., NY (US); Steven L. Hull, Mission, TX (US)

(73) Assignee: Fresenius USA, Inc., Lexington, MA (US)

( * ) Notice: Subject to any disclaimer, the term of this patent is extended or adjusted under 35 U.S.C. 154(b) by 450 days.

(21) Appl. No.: 09/455,735

(22) Filed: Dec. 4, 1999

(51) Int. Cl.[7] ............................................. A61M 31/00
(52) U.S. Cl. ........................ 604/500; 604/174; 604/533; 606/151; 128/912; 24/543; 24/336; 24/339
(58) Field of Search ......................... 604/500, 250, 604/905, 246, 263, 174, 177, 178, 179, 180, 533, 534, 535, 538, 539, 29, 411–416; 606/151, 201–204; 128/912, DIG. 26, 852, 877, 887; 24/543, 336, 339

(56) References Cited

U.S. PATENT DOCUMENTS

| | | | | |
|---|---|---|---|---|
| 408,080 A | * | 7/1889 | Carroll | ........................ 168/45 |
| 593,978 A | * | 11/1897 | Boehm | |
| 1,989,823 A | * | 2/1935 | Raabe | ........................ 173/328 |
| 3,385,299 A | * | 5/1968 | Le Roy | ..................... 24/593.11 |
| 3,473,528 A | * | 10/1969 | Mishkin et al. | .............. 606/218 |
| 3,475,716 A | * | 10/1969 | Laig | ............................. 339/75 |
| 3,494,580 A | * | 2/1970 | Thorsman | ..................... 248/68 |
| 3,971,384 A | * | 7/1976 | Hasson | ........................ 606/218 |
| 4,201,215 A | * | 5/1980 | Crossett et al. | ................ 24/370 |
| 4,333,505 A | * | 6/1982 | Jones et al. | .................. 141/383 |
| 4,340,052 A | * | 7/1982 | Dennehey et al. | ........... 128/247 |
| 4,405,312 A | * | 9/1983 | Gross et al. | ................... 604/29 |
| 4,730,615 A | * | 3/1988 | Sutherland et al. | ........ 24/16 PB |
| 4,955,864 A | * | 9/1990 | Hajduch | ...................... 604/174 |
| 5,356,412 A | * | 10/1994 | Golds et al. | ................... 24/170 |
| 5,356,417 A | * | 10/1994 | Golds | ........................ 24/16 PB |
| 6,051,007 A | * | 4/2000 | Hogendijk et al. | .......... 606/151 |

* cited by examiner

*Primary Examiner*—Brian L. Casler
*Assistant Examiner*—Cris L. Rodriguez
(74) *Attorney, Agent, or Firm*—Gibson, Dunn & Crutcher LLP

(57) ABSTRACT

This invention utilizes a connector holding device to prevent the accidental disconnection of the two halves of a connection device for a fluid connector system.

5 Claims, 3 Drawing Sheets

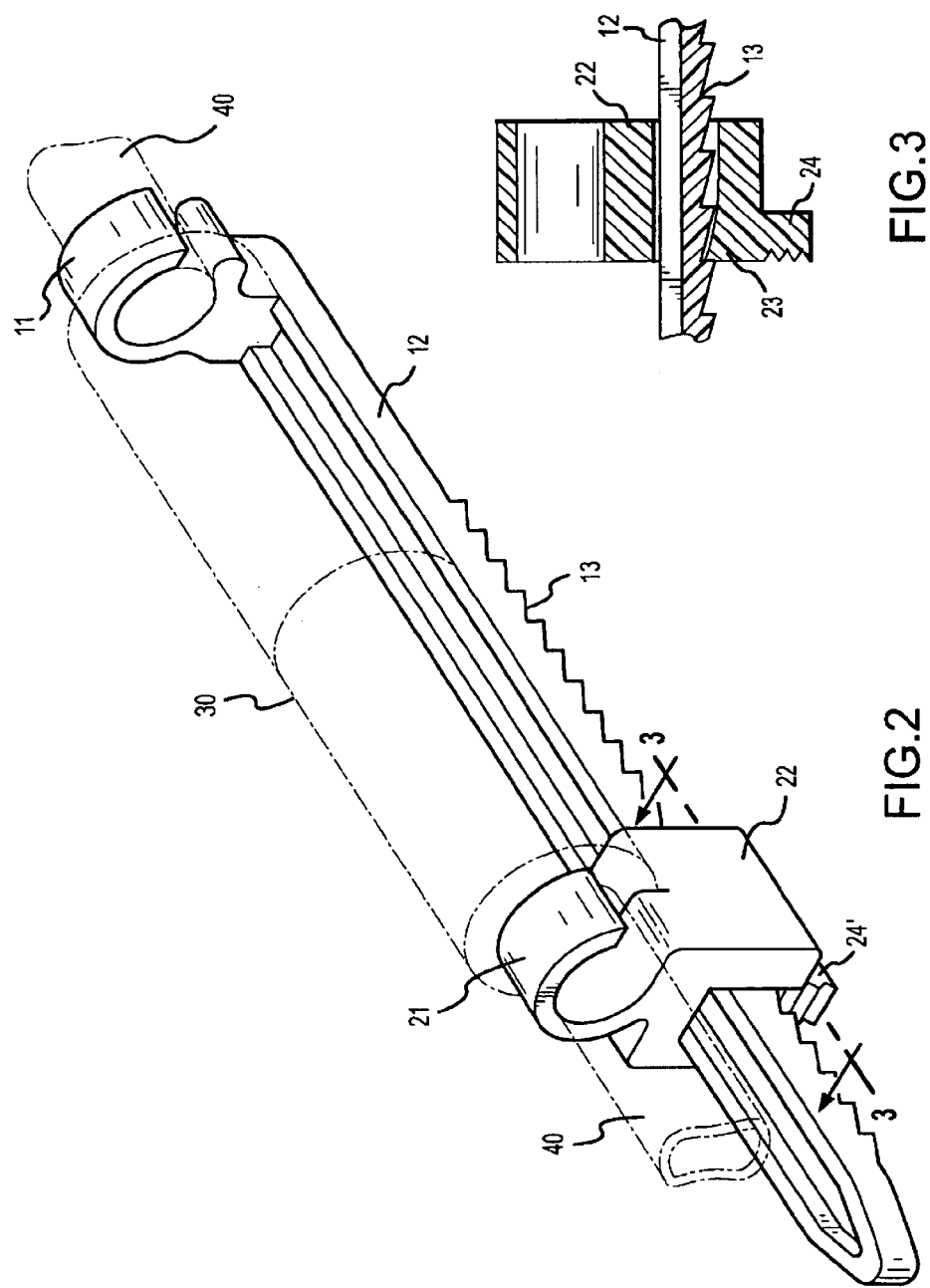

CONNECTOR HOLDER FOR A FLUID CONNECTION SYSTEM

FIELD OF THE INVENTION

The present invention relates to the field of connectors for extracorporeal medical tubing. Such extracorporeal medical tubing is used in dialysis procedures such as peritoneal dialysis and hemodialysis and in a variety of other medical procedures. Extracorporeal procedures are to be distinguished from intracorporeal procedures and uses such as prosthetic implants, urinary catheters and other implantable catheters, shunts and cannulation devices.

BACKGROUND OF THE INVENTION

Many modern medical procedures require the use of tubing sets of varying complexity to withdraw fluid from a patient, or to administer fluid to a patient, or to do both. Such procedures include intravenous feeding, blood transfusions and blood processing, and both peritoneal dialysis and hemodialysis. Typically, a catheter is temporarily or semi-permanently implanted in the patient such as by cannulating a vein in the case of hemodialysis or a catheter is implanted in a peritoneal cavity in the case of peritoneal dialysis. The catheter extends from the implant site to outside the body, where it is connected in some manner to the appropriate tubing set necessary for the procedure that is to be performed.

The configuration and complexity of tubing sets are vastly different depending upon the particular medical procedure for which they are designed and also depending on the manufacturer of the other extracorporeal elements used in the procedure. For example, a hemodialysis tubing set is much different from a peritoneal dialysis tubing set because of the different nature and requirements of hemodialysis as compared to peritoneal dialysis, and a peritoneal dialysis tubing set made by one manufacturer for use with its peritoneal dialysis cycler machine may be much different from a peritoneal dialysis tubing set made by another manufacturer for use with the other manufacturer'peritoneal dialysis cycler machine.

In hemodialysis, the patient'blood is cleansed by drawing it out of the patient though a catheter and passing it through an artificial kidney. The artificial kidney includes a semi-permeable membrane which removes impurities and toxins by a process of diffusion. The purified blood is then returned to the patient. A hemodialysis tubing set is used to transport the blood between the catheters and the artificial kidney. Patients in hemodialysis treatment typically require treatment several times a week for several hours each time.

In peritoneal dialysis, a peritoneal dialysis solution is infused into the patient'peritoneal cavity and allowed to reside there for a "dwell time" during which blood impurities diffuse through the puitoneal membrane into the dialysis solution. The dialysis solution with the collected impurities is then removed from the peritoneal cavity and discarded. In Continuous Ambulatory Peritoneal Dialysis ("CAPD") the infusion of dialysis solution into and out of the peritoneal cavity is accomplished throughout the day while the patient goes about a fairly normal routine. In Intermittent Peritoneal Dialysis ("IPD") large amounts of dialysis solution (up to 40 liters) are cycled through the patient'peritoneal cavity over a 4 to 24 hour period. In Continuous Cycling Peritoneal Dialysis ("CCPD") the dialysis treatment is more or less continuous, with dwell times of 3 to 4 hours at night. Then, throughout the waking time of the patient, a single dose of dialysis solution is retained within the patient.

In both IPD and CCPD an automated dialysis apparatus operates in generally the same manner. The dialysis solution and "tubing administration set" or simply "tubing set" is integrated with the valving, heating and control functions associated with the automated apparatus. In many of the systems, premeasured amounts of dialysis solution are either pumped or delivered by gravity flow to a heating station. At the heating station the solution is warmed to body temperature in order to prevent the uncomfortable sensation of introducing room temperature or cooler solution into the peritoneal cavity. The warmed solution is then allowed to enter the patient via a catheter implanted in the patient'peritoneal cavity. After a period of time (the "dwell period"), the solution is drained from the patient into a spent solution container.

In IPD, a large amount of solution is cycled in this manner over a relatively short period of time. Once treatment is completed, the patient is unencumbered for at least a few days. A disadvantage is the large amount of dialysis solution that must be utilized. Bags cumulating to at least 40 liters of solution can be difficult to lift for a patient in a weakened condition.

In CCPD and CAPD methods, the same efficiency of results is obtained by increasing the dwell time of the dialysis solution within the peritoneal cavity. The total amount of solution required can therefore be significantly reduced. The obvious disadvantage, is that there is no "down time" for the treatment.

Many of the tubing sets used with these dialysis procedures or with other medical procedures involving extracorporeal treatment of fluid, use connection devices to connect two pieces of tubing together. For example, a hemodialysis patient or a peritoneal dialysis patient will often have a semi-permanent implanted catheter in the vascular system or peritoneal cavity, respectively, which extends to outside the patient. The exterior end may be attached to a tubing segment which in turn is usually attached to half of the connection device. The other half of the connection device is attached to another tubing segment which in turn may be attached to a pump or bag of fluid.

The system used for a medical procedure may require several connection devices that connect several tubing segments, thereby permitting fluid flow through the entire system and the patient. When it is time to begin the procedure, the two halves of each connection device are connected so that fluid can flow from one tubing segment to the other tubing segment. It is important for the connection devices between the tubing segments to be mechanically strong and secure to prevent accidental disconnection and maintain fluid flow during the procedure. For example, the two halves of the connection device usually have a set of interlocking threads and the mechanical connection between the two halves of the connection device is achieved by screwing the two halves together. This simply requires that one of the halves be rotated about its axis in relation to the other while a slight force is applied urging the two halves together. Once the connections have all been made, fluid can flow throughout the system and the medical procedure can begin.

To further prevent accidental disconnection of the connection device and maintain fluid flow through the system during the medical procedure, it is not uncommon for a medical practitioner to strengthen the connection device between two tubing segments by taping the two halves of the connection device together with medical tape. In the case of a connection device with two halves that have interlocking threads, this would help prevent the two halves from unscrewing or coming apart during the procedure.

However, taping together the two halves of the connection device can take time and is not necessarily easy to do. Furthermore, while the tape is effective in preventing accidental disconnection, this is not what medical tape was designed for and it is difficult and messy to remove the medical tape when it is necessary to disconnect the tubes after the procedure is completed.

Therefore, there still remains a need for an inexpensive connector holding device that is easy to connect and disconnect and will back up the connection device to prevent accidental disconnection of the tubing segments and maintain the connection so that fluid can flow through the tubing set during treatment.

SUMMARY OF THE INVENTION

The present invention is a connector holding device that has particular but not exclusive application in peritoneal dialysis and hemodialysis tubing sets. The holding device includes a first tube holder which has a means for holding a tubing segment on one side of a connection device and a second tube holder which has a means for holding a second tubing segment on the other side of the connection device, the two tube holders being engagable with each other so that the connection device can not separate.

In one embodiment, both the first tube holder and the second tube holder each have a semi-cylindrical clip that can circumferentially partially surround the tube and hold it in place. The first tube holder and the second tube holder are engagable through a locking means. In one embodiment, the first tube holder has an arm that extends parallel to the first tubing segment, which is being held by the first tube holder, and is longer than the length of the connection device when the two halves of the connection device are engaged. The arm has one or more notches along at least one of its edges. The second tube holder has a hole in its base through which the arm on the first tube holder can be inserted, thereby slidably attaching the second tube holder to the first tube holder. The second tube holder also has at least one tooth which can engage the notches on the arm of the first tube-holder, thereby preventing the second tube holder from sliding away from the first tube holder along the arm. The tooth has a knob on its end so that a user can apply pressure to one side of the knob, thereby pulling back the tooth, and then slide the second tube holder along the arm of the first tube holder away from the first tube holder without the tooth engaging the notches on the arm.

The connector holding device is applied to the fluid connection system after the two halves of the connection device are engaged. The two halves of the connection device (the first tubing segment connector and the second tubing segment connector) are each attached to a tubing segment. The connection device often has threads and the connection device is often connected by screwing the two halves together. This simply requires that one of the halves be rotated about its axis in relation to the other while a slight force is applied urging the two halves together. Similarly, the connection device is then disconnected by unscrewing the two halves. This is done by rotating one of the halves around its axis while a slight force is applied to pull the two halves apart.

After a connection has been made with a connection device, the connection holding device is placed around the two halves of the connection device to maintain the connection and fluid flow between the two tubing segments. The second tube holder can initially be in a position along the arm of the first tube holder so that the distance between the first tube holder and the second tube holder is greater than the length of the connection device when the two halves of the connection device are engaged. The first tube holder and the second tube holder are then placed around the tubing segments that extend from either half of the connection device. After both tube holders have engaged the tubing segments, the user can then slide the second tube holder along the arm of the first tube holder toward the first tube holder until both tube holders are resting next to the ends of the connection device. The locking means keeps the second tube holder in place and prevents it from sliding along the arm of the first tube holder away from the first tube holder. Since the connection holder device holds the tubing segments on either side of the connector and the second tube holder is locked into place on the arm of the first tube holder, the second tube holder cannot slide away from the first tube holder. This prevents the two halves of the connection device from being unscrewed or disconnected while the connection holder device is in place. As long as the second tube holder is locked into position along the arm of the first tube holder, the connection is maintained because the connection device cannot be accidentally disconnected.

When the treatment is over, the connection holder device can be removed by cutting the arm of the first tube holder so that the second tube holder is no longer locked in place. Alternatively, the locking means on the connection holder device may have a release mechanism, such as the knob on the end of the tooth, that allows the connection holder device to be removed by releasing the locking means. This can be accomplished by placing pressure on the knob of the tooth so that the tooth will no longer engage the notches on the bottom of the arm of the tube holder and sliding the second tube holder along the arm away from the first tube holder. Once the second tube holder is separated far enough away from the first tube holder, the tubing segments attached to either half of the connection device can be removed from the first and second tube holders. The user is then free to unscrew or disconnect the two halves of the connection device.

BRIEF DESCRIPTION OF THE DRAWINGS

FIG. 2 shows the first tube holder and second tube holder slidably attached and holding the connection device in place.

FIG. 3 shows a cut away view of the side of the second tube holder engaging the arm of the first tube holder.

DETAILED DESCRIPTION OF THE INVENTION

Figure 1:
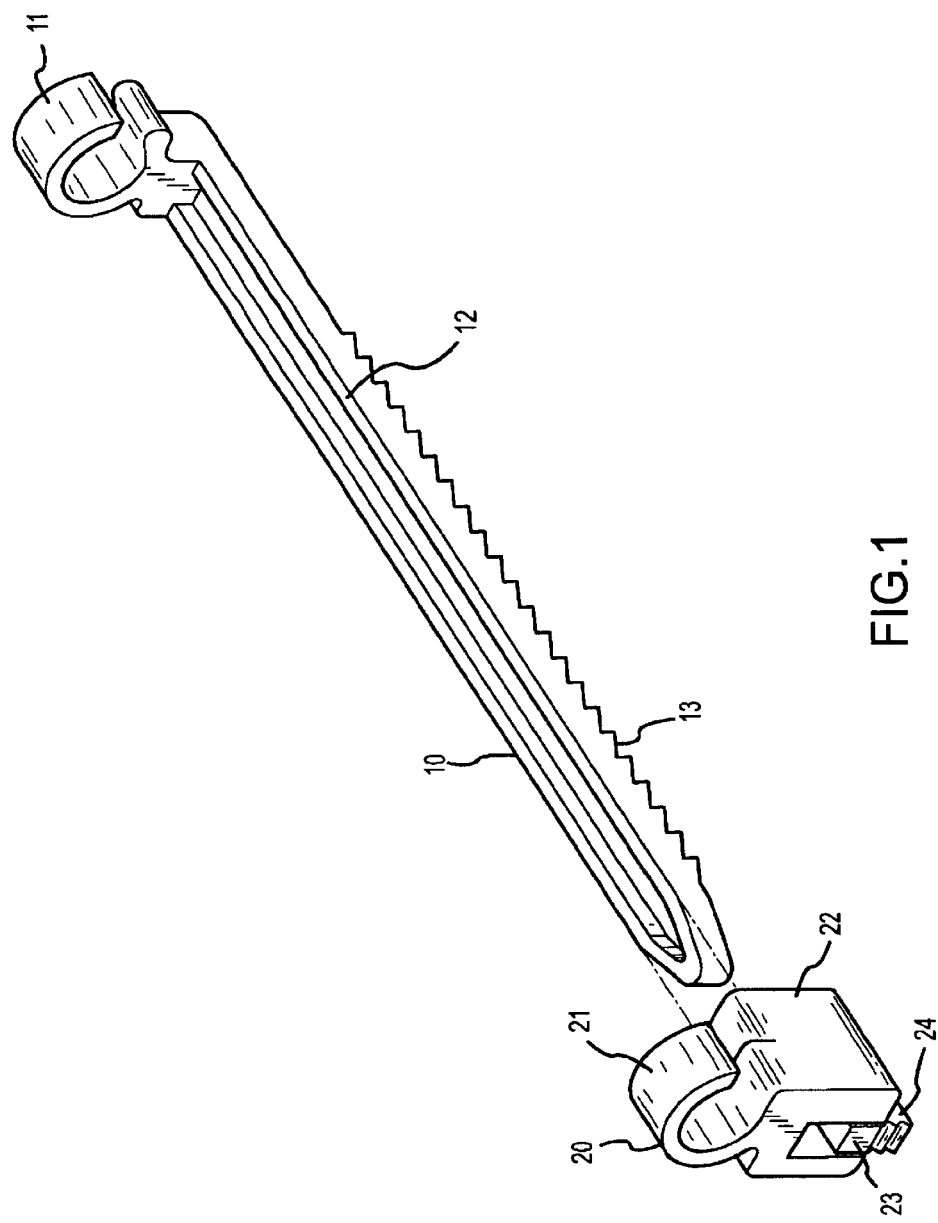
FIG. 1 shows the first tube holder and the second tube holder before they are slidably attached.

The present invention includes a first tube holder which has a means for holding a tubing segment on one side of a connection device and a second tube holder which has a means for holding a second tubing segment on the other side of the connection device, the two tube holders being engagable with each other so that the connection device cannot separate.

As shown in FIGS. 1–4, one embodiment of this invention is made of a first tube holder 10 and a second tube holder 20. The first tube holder 10 includes a means for holding or engaging a tubing segment 40 such as a semi-cylindrical shaped clip 11. The second tube holder 20 also include a means for holding or engaging a tubing segment 40 such as a semi-cylindrical shaped clip 21. These clips 11, 21 can extend circumferentially partially around the tubing segment 40, and they can be made of an inexpensive plastic or some other rigid material. When placed around a tubing segment 40, the clip 11 of the first tube holder 10 and the clip 21 of the second tube holder 20 hold the tubing segments 40 in place.

The first tube holder 10 also has a means for engaging the second tube holder 20 so that the first tube holder 10 and the second tube holder 20 are held in place. In one embodiment, as shown in FIGS. 1–4, the first tube holder 10 has an arm 12 that is attached to the clip 11. The arm 12 extends from the clip 11 parallel to the tubing segment 40 that is being held by the clip 11. The arm 12 must be longer than the length of the connection device 30 when the two halves of the connection device 30 are engaged. In this embodiment, the arm 12 has one or more notches 13 along its bottom edge that work with at least one tooth 23 on the second tube holder 20 to prevent the second tube holder 20 from sliding along the arm 12 of the first tube holder 10 away from the clip 11 of the first tube holder 10. Like the first tube holder 10 and the second tube holder 20, the arm 12 can be made of an inexpensive plastic or some other rigid material.

In addition to the means for holding or engaging a tubing segment such as the semi-cylindrical clip 21, the second tube holder 20 also has a means for engaging the first tube holder 10. In the pictured embodiment of this invention, the base 22 of the second tube holder 20 has a hole through it so that the second tube holder 20 can be slidably attached to the first tube holder 10 by inserting the arm 12 of the first tube holder 10 through the hole in the base 22 of the second tube holder 20. The second tube holder 20 can then slide along the arm 12 of the first tube holder 10 toward the clip 11 of the first tube holder 10.

Finally, the second tube holder 20 has a means for locking the second tube holder 22 in place and preventing the second tube holder 22 from sliding along the arm 12 of the first tube holder 10 away from the clip 11 of the first tube holder 10. In the embodiment pictured in FIGS. 1–4, this locking means is comprised of at least one tooth 23 that slightly extends into the hole in the base 22 of the second tube holder 20. The tooth 23 is attached to the base 22 of the second tube holder 20 and angles up so that the opening on the side of the base 22, where the arm 12 of the first tube holder 10 exits the hole in the base 22 of the second tube holder 20 is smaller than the opening on the side of the base 22 of the second tube holder 20 where the arm 12 of the first tube holder 10 enters the hole in the base 22 of the second tube holder 20. When the second tube holder 20 is slidably attached to the first tube holder 10, the second tube holder 20 can be moved along the arm 12 of the first tube holder 10 toward the clip 11 of the first tube holder 10. However, the second tube holder 20 cannot then be moved away from the clip 11 of the first tube holder 10 because the tooth 23 on the second tube holder 20 will engage one of the notches 13 in the bottom of the arm 12 of the first tube holder 10. This is shown in FIG. 3.

Figure 4:
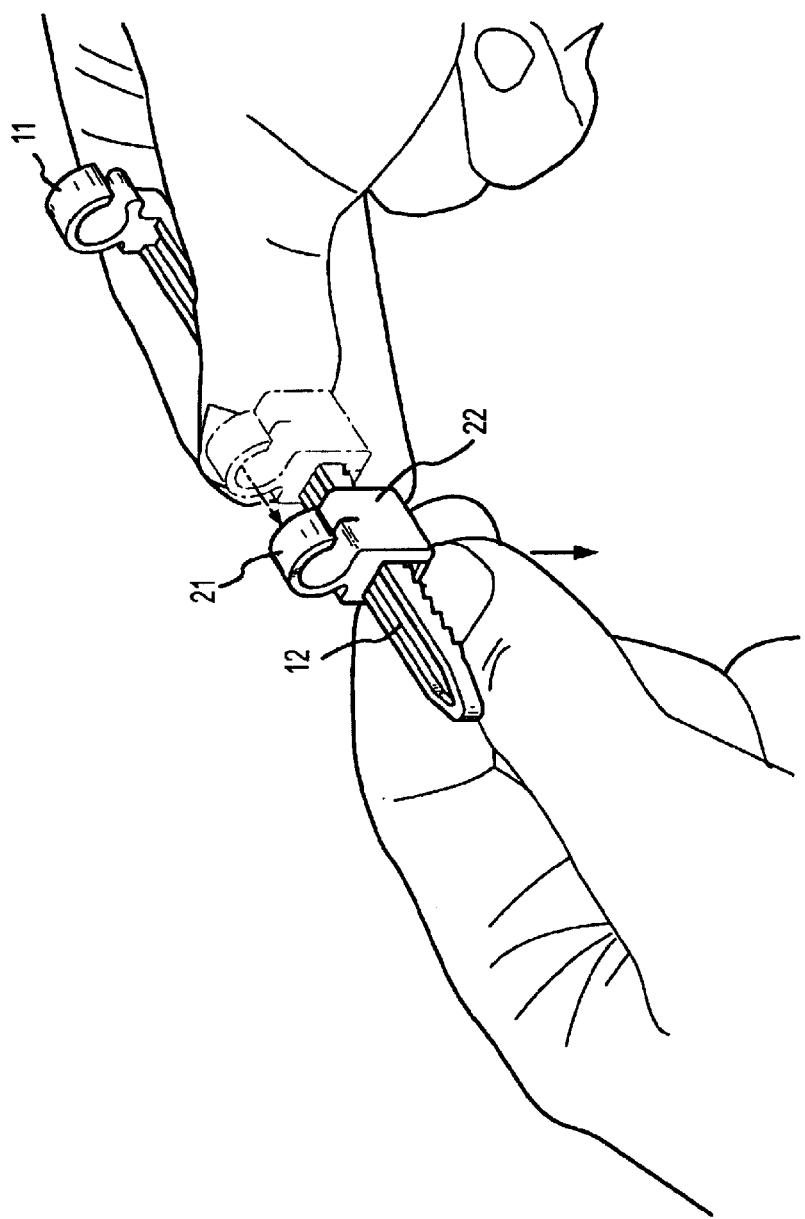
FIG. 4 shows how the locking mechanism can be released so that the second tube holder can slide along the arm of the first tube holder away from the clip of the first tube holder.

The tooth 23 may also have a knob 24 on its end as a release mechanism. When pressure is applied to the knob 24 so that the tooth 23 is pulled away from the hole in the base 22 of the second tube holder 20, the second tube holder 20 can be moved along the arm 12 of the first tube holder 10 away from the clip 11 of the first tube holder 10 until the pressure on the knob 24 is released and the tooth 23 once again engages one of the notches 13 in the arm 12 of the first tube holder 10. This allows the locking means to be released as shown in FIG. 4.

The clip 11 of the first tube holder 10 and the clip 21 of the second tube holder 20 should then engage the tubing segments 40 that extend from either end of the connection device 30. Once the clip 11 for the first tube holder 10 and the clip 21 for the second tube holder 20 have engaged the tubing segments 40 at either end of the connection device 30, the user can then slide the second tube holder 20 along the arm 12 of the first tube holder 10 toward the clip 11 of the first tube holder 10 until the clip 11 of the first tube holder 10 and the clip 21 of the second tube holder 20 are both resting adjacent to the ends of the connection device 30. The locking means then keeps the second tube holder 20 from sliding along the arm 12 of the first tube holder 10 away from the clip 11 of the first tube holder 10, thereby holding the connection device 30 together. This prevents accidental disconnection of the connection device 30.

Many medical procedures use tubing sets. In use, the connection holding device can be applied at each place where a connection device is used to connect two tubing segments, thereby maintaining these connections so that fluid can flow through the tubing set. The connection device will usually have two halves that can be connected together. Each half of the connection device will be attached to a tubing segment (the first tubing segment connector and the second tubing segment connector). When the two halves of the connection device are engaged, fluid can flow from one tubing segment to the other tubing segment without leaking from the system. The two halves of the connection device have some means of connection. For example, interlocking threads are sometimes located on the two halves of the connection device so that they can be screwed together. This is done by rotating one of the halves around its axis while a slight force is applied to push the two halves together. Once the two halves of the connection device are connected, the connector holding device can then be placed around the connection device to prevent the two halves of the connection device from accidentally unscrewing or coming apart.

The connector holding device is applied to the fluid connection system after the two halves of the connection device 30 are engaged. The second tube holder 20 can initially be in a position along the arm 12 of the first tube holder 10 so that the distance between the clip 11 of the first tube holder 10 and the clip 21 of the second tube holder 20 is greater than the length of the connection device 30 when the two halves of the connection device 30 are engaged. The clip 11 of the first tube holder 10 and the clip 21 of the second tube holder 20 are then placed around the tubing segments 40 extending from the two halves of the connection device 30, one on either side of the connection device 30. This is done by setting one tubing segment 40 against the open side of the clip 11 of the first tube holder 10. The tubing segment 40 coming out of the other end of the connection device 30 should then be set against the open side of the clip 21 of the second tube holder 20 so that the arm 12 of the first tube holder 10 extends between the first tube holder 10 and the second tube holder 20, along the side of the connection device 30. When enough pressure is applied to the side of the tubing segment 40 that is opposite the side of the tubing segment 40 that has been set against the open side of each clip 11, 21, the tubing segment 40 will slip into the clip 11, 21 through the open side of the clip 11, 21. Each clip 11, 21 will then nearly surround the tubing segment 40 as it extends circumferentially partially around the tubing segment 40 and hold it in place. This should be done with both clips 11, 21 so that the tubing segments 40 coming out of each end of the connection device 30 are each being held by one of the two clips 11, 21 with the arm 12 of the first tube holder 10 extending between the two clips 11, 21.

After the clip 11 of the first tube holder 10 and the clip 21 of the second tube holder 20 are both holding a tubing segment 40 on either side of the connection device 30, the user can then slide the second tube holder 20 toward the clip 11 of the first tube holder 10 along the arm 12 of the first tube holder 10 until the clip 11 of the first tube holder 10 and the clip 21 of the second tube holder 20 are both holding a tubing segment 40 adjacent to either end of the connection device 30 (as shown in FIG. 2).

The tooth 23 that is attached to the base 22 of the second tube holder 20 will engage one of the notches 13 in the arm 12 of the first tube holder 10 and prevent the second tube holder 20 from sliding along the arm 12 of the first tube holder 10 away from the clip 11 of the first tube holder 10. Since the two halves of the connection device 30 are usually connected by threads, the connection device 30 is disconnected by unscrewing the two halves. This is done by rotating one of the halves around its axis while a slight force is applied to pull the two halves apart. When the first tube holder 10 and the second tube holder 20 are holding the tubing segments 40 on either side of the connection device 30 and the second tube holder 20 cannot slide along the arm 12 of the first tube holder 10 away from the clip 11 of the first tube holder 10 because the tooth 23 in the base 22 of the second tube holder 20 catches on one of the notches 13 along the arm 12 of the first tube holder 10, the connection device 30 is prevented from disconnecting until the connection holder device is removed from the tubing system. This maintains the connection and prevents accidental disconnection of the connection device 30.

When the treatment is over, the connection holder device can be removed in at least two different ways. First, the arm 12 on the first tube holder 10 can be severed. Then the tubing segments 40 can be removed from the clips 11, 21 by applying pressure to the side of the tubing segments 40 that are opposite the opening in the clips 11, 21. The tubing segments 40 should then slide out of the clips 11, 21 and the two pieces of the connection holder device can be discarded.

Alternatively, the connection holder device can be removed by applying pressure to the knob 24 on the tooth 23 of the second tube holder 20 so that the tooth 23 is pulled away from the notches 13 along the bottom of the arm 12 of the first tube holder 10. As shown in FIG. 4, the second tube holder 20 can then be moved along the arm 12 of the first tube holder 10 away from the clip 11 of the first tube holder 10 without the tooth 23 catching on one of the notches 13 on the bottom of the arm 12 of the first tube holder 10. The tubing segments 40 can then be removed from the clips 11, 21 by applying pressure to the side of the tubing segments 40 that are opposite the opening in the clips 11, 21. The tubing segments 40 should then slide out of the clips 11, 21 and the connection holder device can be reused on another tubing system. The user is then free to disconnect the connection device 30.

The connection holder device can be used to secure each connection device in a tubing set, thereby maintaining each connection so that fluid can flow in the system. As the tubing set is assembled, the connection holder device should be applied to each connection device. After the medical procedure is complete and the tubing set is being disassembled, the connection holder device should be removed from each connection device.

We claim:

1. A device for maintaining a connection between a first tubing segment including a first tubing segment connector and a second tubing segment including a second tubing segment connector, the first tubing segment connector and the second tubing segment connector being connectable to establish fluid connection from the first tubing segment through the second tubing segment comprising: a first tube holder for holding the first tubing segment; and a second tube holder for holding the second tubing segment, the first tube holder being engagable with the second tube holder, wherein said first tube holder gas an arm that is parallel to the first tubing segment, said arm being engagable by the second tube holder, and wherein said arm has one or more notches along at least one of its edges, and said second tube holder has one or more teeth slidably engagable with said notches.

2. A device according to claim 1, wherein said notches and teeth are configured to allow the arm to slide into but not out of the second tube holder.

3. A device according to claim 2, wherein said second tube holder has a release mechanism to allow the arm to slide out of the second tube holder.

4. A device according to claim 3, wherein said release mechanism is a knob on the second tube holder.

5. A method for maintaining one or more connections in a tubing set, comprising the steps of: attaching a first tubing segment with a first tubing segment holder having an arm extending parallel to the first tubing segment, said arm having a set of longitudinal notches having one or more teeth slidably engagable with said notches; and slidably engaging said arm with said teeth whereby fluid communication is established and maintained between the first tubing segment and the second tubing segment.

* * * * *